United States Patent [19]

Keiser

[11] 4,050,310
[45] Sept. 27, 1977

[54] EXERCISING APPARATUS

[76] Inventor: Dennis L. Keiser, 14634 E. Annadale Ave., Sanger, Calif. 93657

[21] Appl. No.: 667,611

[22] Filed: Mar. 17, 1976

[51] Int. Cl.² .......................... G01L 5/02; A63B 21/20
[52] U.S. Cl. ...................................... 73/379; 272/130
[58] Field of Search ................... 73/379; 272/130, 134

[56] References Cited

U.S. PATENT DOCUMENTS

| | | | |
|---|---|---|---|
| 3,451,271 | 6/1969 | Knoblauch | 73/379 X |
| 3,481,198 | 12/1969 | Williams | 73/379X |
| 3,848,467 | 7/1974 | Flavell | 73/379 |
| 3,896,672 | 7/1975 | Henson et al. | 73/379 |

FOREIGN PATENT DOCUMENTS 405,617   4/1967   Australia .............................. 272/130

*Primary Examiner*—Daniel M. Yasich
*Attorney, Agent, or Firm*—Huebner & Worrel

[57] ABSTRACT

An exercising apparatus having a member adapted to receive the application of muscular force thereagainst, a frame mounting the member for movement along a path of travel, a mechanism for resisting movement of the member along the path of travel, and a recording device connected to the mechanism for recording the force applied to the member in relation to the position of the member along the path.

12 Claims, 15 Drawing Figures

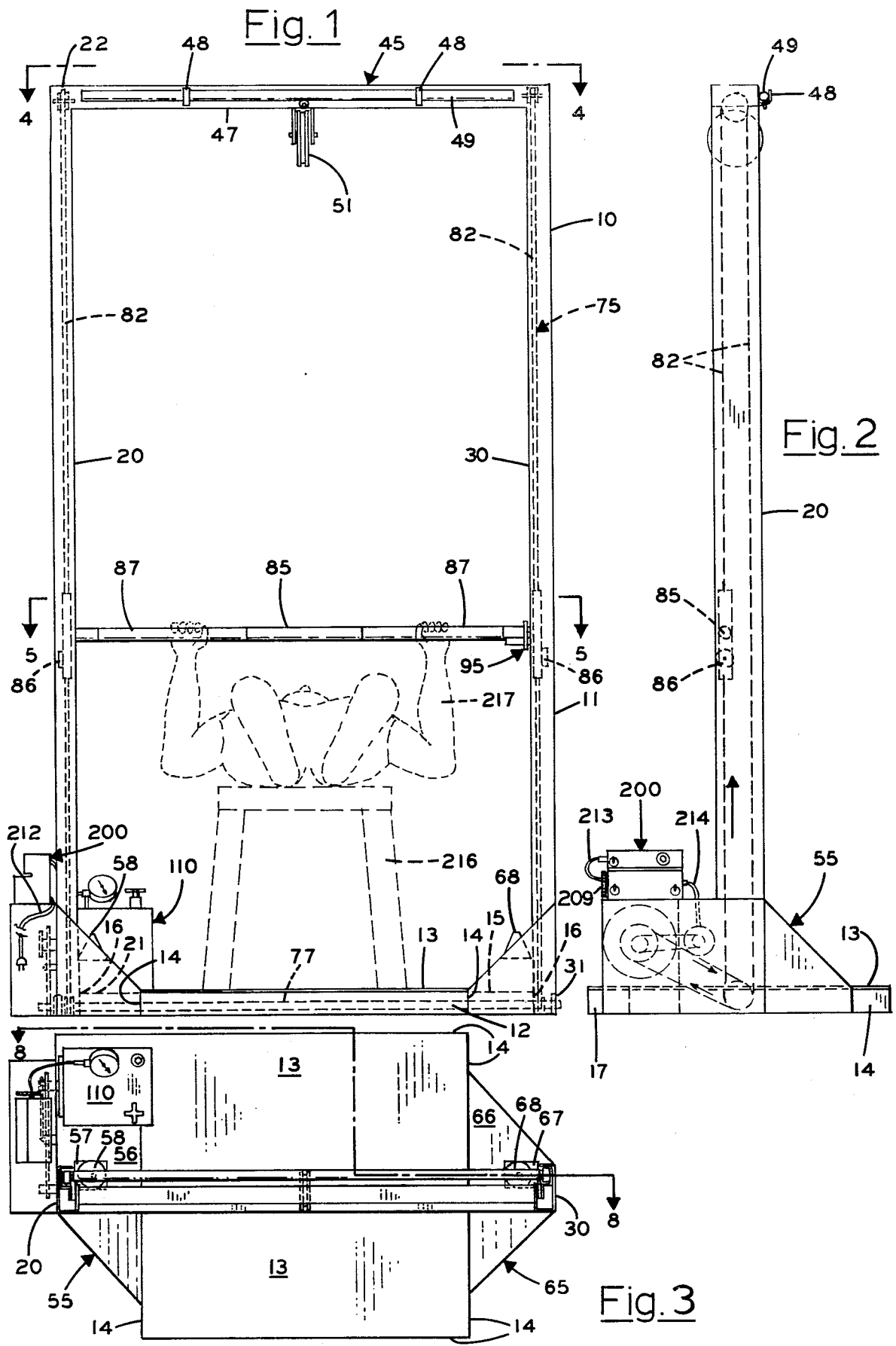

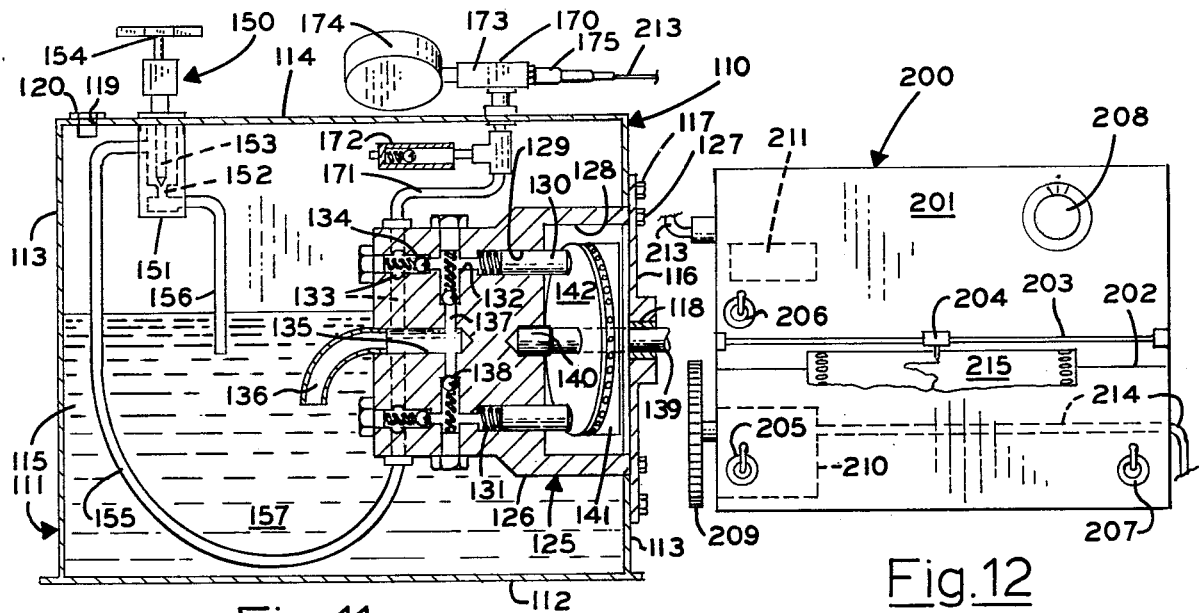
Fig. 11
Fig. 12
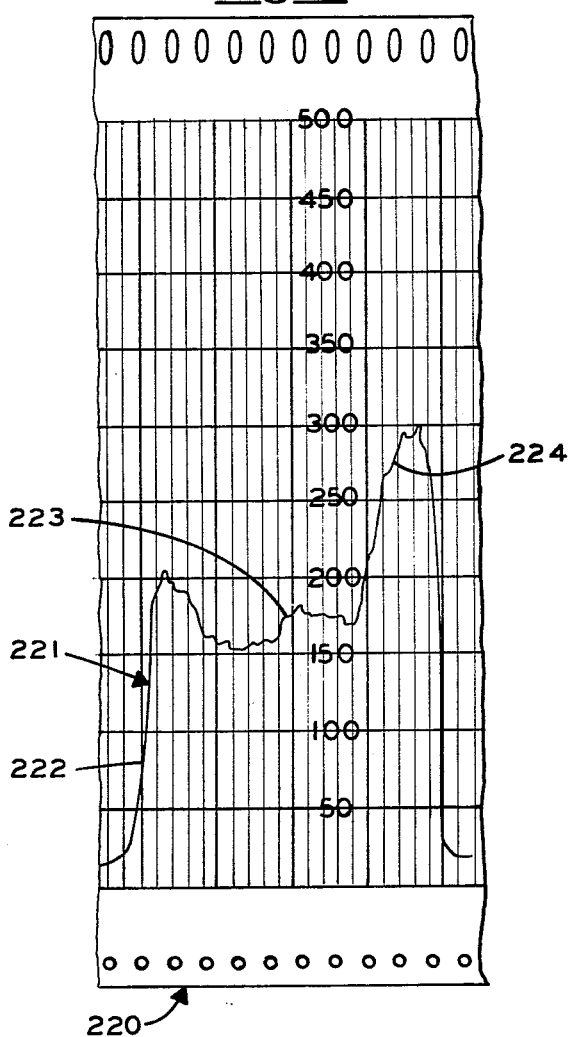
Fig. 13
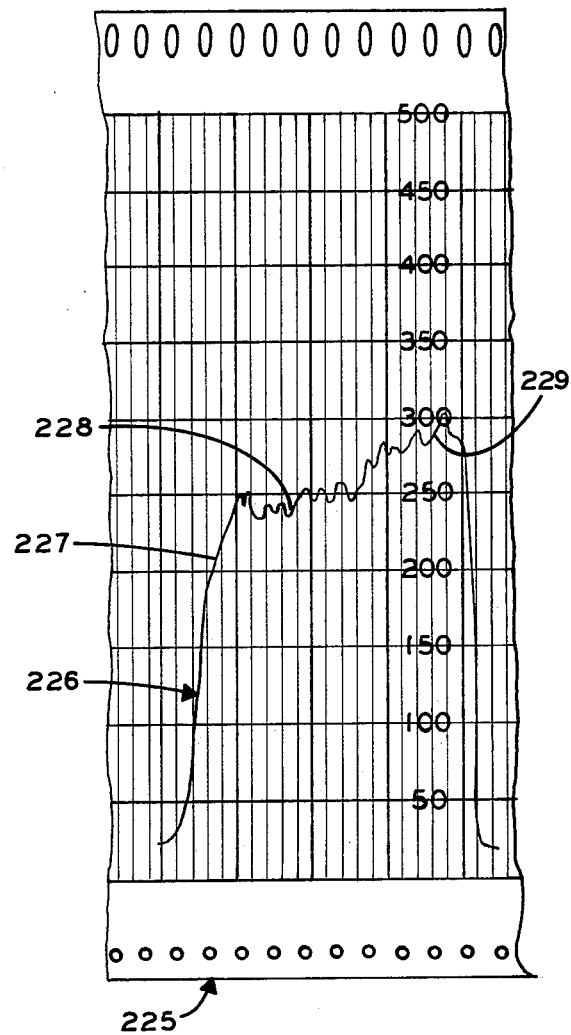
Fig. 14

EXERCISING APPARATUS

BACKGROUND OF THE INVENTION

1. Field Of The Invention:

The present invention relates to an exercising apparatus and more particularly to such an exercising apparatus which is operable by the application of muscular force on an exercising member in a manner similar to that for a barbell, but in which the resistance of the apparatus varies in direct relation to the force applied to the member permitting the operator to work at his maximum ability throughout the lifting stroke; to such an apparatus which permits the operator to record the force exerted on the member in relation to the position of the member in the stroke; and to such an apparatus which possesses a convenience, safety and adaptability of operation not heretofore achieved in exercising devices at moderate costs.

2. Description Of The Prior Art:

It has long been known to use a variety of types of weight devices, such as barbells, to develop muscle structure in the arms, shoulders, back and other portions of the human body for therapeutic and/or athletic purposes. Such devices are cumbersome in use as well as dangerous in view of the lack of any satisfactory means for preventing the accidental dropping of such devices.

For these reasons as well as others, a variety of types of exercising devices have been developed to provide a measure of safety in operation and to permit an adaptability to a variety of types of uses not possible with barbell type devices. Such prior art exercising devices are typified by Sollenberger U.S. Pat. No. 3,359,802; the Keropian U.S. Pat. No. 3,374,675; the Perrine U.S. Pat. No. 3,465,592; the Gilstrap Pat. No. 3,606,318; the Phillips et al. U.S. Pat. No. 3,702,188; the Perrine U.S. Pat. No. 3,784,194; the Bradley et al. U.S. Pat. No. 3,785,644; and the Spector Pat. No. 3,834,696.

While some prior art devices have endeavored to provide a means for registering the force applied against the work member of the apparatus as an indication of the strength exerted by the operator, such devices typically use simple pressure gauges to register fluid pressure created by operation of the exercising device. Most such devices require movement of a work member along a path of travel which is unnatural for the operator, such as, for example, an awkward arcuate path of travel. Some attempts have also been made to provide a written record of the force exerted such as through the use of a strip chart recorder.

While prior art exercising devices may possess one or more advantageous features, insofar as the applicant is aware, there is no prior art device which permits the operator to control the effective resistance to the force exerted throughout an exercising stroke and to produce a physical record of the force exerted in relation to all positions of the exercising member throughout the entire length of that stroke. Such a record permits a virtually instantaneous clinical analysis of the strength of the operator throughout the stroke for purposes of the analysis of muscle development and the coordination of an exercising program keyed to development of the strength of the operator at the particular point in the stroke where it is most desirable. Thus, for example, in physical therapy it may be desirable to increase the strength of arm muscles when the arm is in a given attitude. Similarly, in weight lifting it is often important to develop the strength of the weight lifter through the weakest point of the lifting stroke which is usually approximately midway through the lifting stroke.

Therefore, it has long been known that it would be desirable to have an exercising apparatus which allows the operator to vary the effective resistance against which the exercising force is applied at the control of the operator throughout the exercising stroke, which affords a safety and facility of use compatible with wide and prolonged usage and which automatically produces a physical record of the force exerted by the operator at all points throughout the exercising stroke.

SUMMARY OF THE INVENTION

Therefore, it is an object of the present invention to provide an improved exercising apparatus.

Another object is to provide such an apparatus which permits exercising to be accomplished in a manner compatible with normal muscular exertion.

Another object is to provide such an exercising apparatus which permits resistance to be encountered in only a single direction along the path of travel of a work member and unweighted, free-wheeling movement in the opposite direction along the path of travel for rapid return to a "start" position.

Another object is to provide such an exercising apparatus which possesses a safety of operation not heretofore achieved in prior art devices.

Another object is to provide such an exercising apparatus which can be employed in a variety of types of exercises without modification and is readily modifiable to permit a still greater number of exercises to be performed.

Another object is to provide such an exercising apparatus which possesses a smoothness of operation with a simplicity of structure so as to insure both comfortable and dependable operation.

Another object is to provide such an exercising apparatus which provides immediate resistance to movement of a work member in a direction along the path of travel without the time lag conventionally encountered in exercising devices between the initiation of movement and the application of resistance or loading.

Another object is to provide such an exercising apparatus which automatically produces a record of the force exerted in the exercising operation.

Another object is to provide such an exercising apparatus which produces a physical record in the form of a chart registering the force applied to a work member at all points along the path of travel without respect to the speed of operation and which can be employed in developing strength at any particular point of muscular extension along the path of travel.

Another object is to provide such an exercising apparatus which employs a recording device in combination with a selector mechanism capable of being adjusted to select the scale against which the operator's force exerted is recorded.

Another object is to provide such an exercising apparatus which can be adjusted to control the resistance against which the operator must work in exercising.

Further objects and advantages are to provide improved elements and arrangements thereof in an apparatus for the purposes described which is dependable, economical, durable and fully effective in accomplishing its intended purposes.

BRIEF DESCRIPTION OF THE DRAWINGS

FIG. 1 is a front elevation of the exercising apparatus of the present invention with an operator shown in dashed lines in a representative position for operation of the apparatus.

FIG. 2 is a side elevation of the apparatus.

FIG. 3 is a top plan view of the apparatus.

FIG. 11 is a longitudinal vertical section of the pump assembly of the apparatus of the present invention.

FIG. 12 is a front elevation of the strip chart recorder of the apparatus of the present invention.

FIG. 13 is a fragmentary plan view of a portion of a strip chart representative of one produced using the apparatus.

FIG. 14 is a fragmentary plan view of a portion of a second strip chart representative of one produced using the apparatus.

DESCRIPTION OF THE PREFERRED EMBODIMENT

Figure 8:
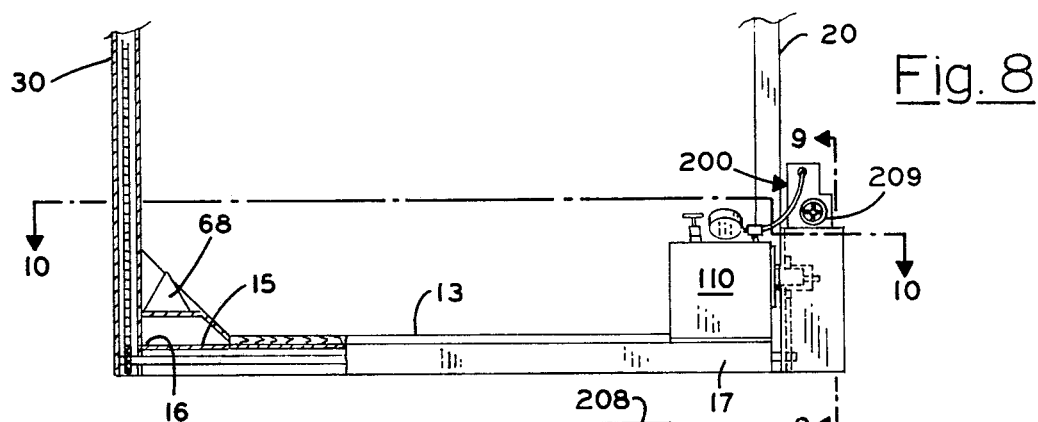
FIG. 8 is a fragmentary vertical section taken on line 8—8 in FIG. 3.
Figure 10:
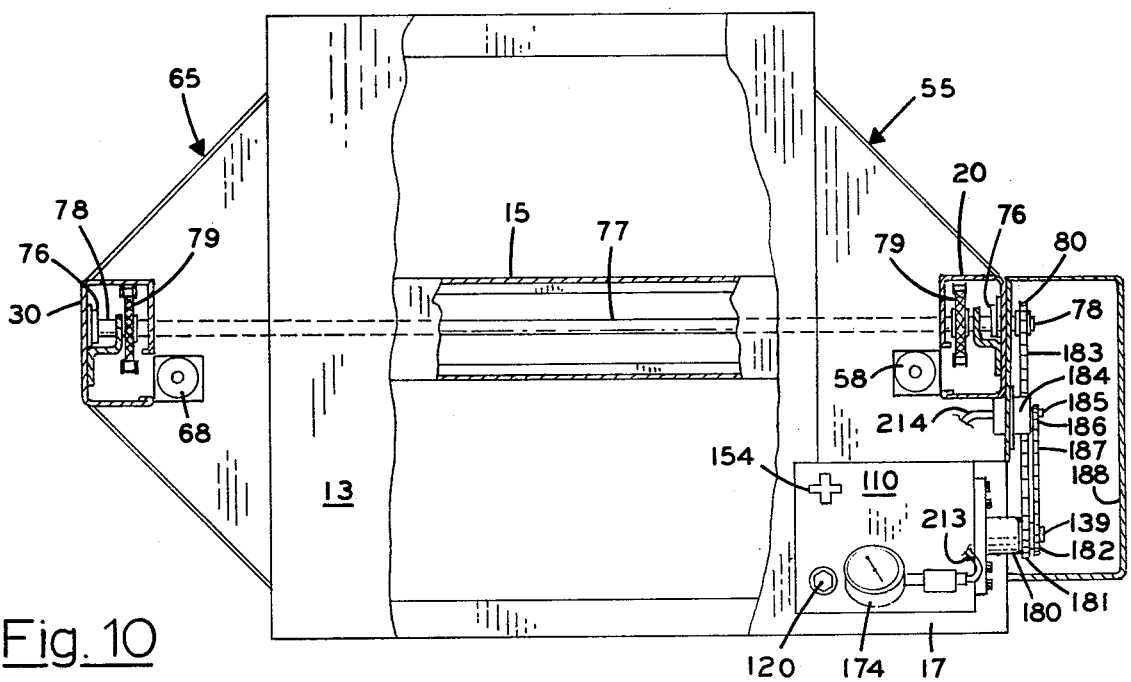
FIG. 10 is a somewhat enlarged fragmentary horizontal section taken on line 10—10 in FIG. 8.

Referring more particularly to the drawings, the exercising apparatus of the present invention is generally indicated by the numeral 10 in FIG. 1. The apparatus has a rigid frame 11 having a substantially rectangular base or platform 12. The platform is adapted to be rested on a suitable supporting surface, such as a floor, and has a floor surface 13 and opposite sides 14. The frame 11 includes a transverse channel member 15 which is mounted on and extends transversely through the platform 12 and outwardly through the sides 14 of the platform, as best shown in FIGS. 1, 8 and 10. The channel member has opposite ends 16 individually extending laterally of the sides of the platform corresponding distances. A pump platform 17 forms an integral part of the platform 12 extending laterally from the side 14 thereof on the left, as viewed in FIG. 3.

Figure 4:
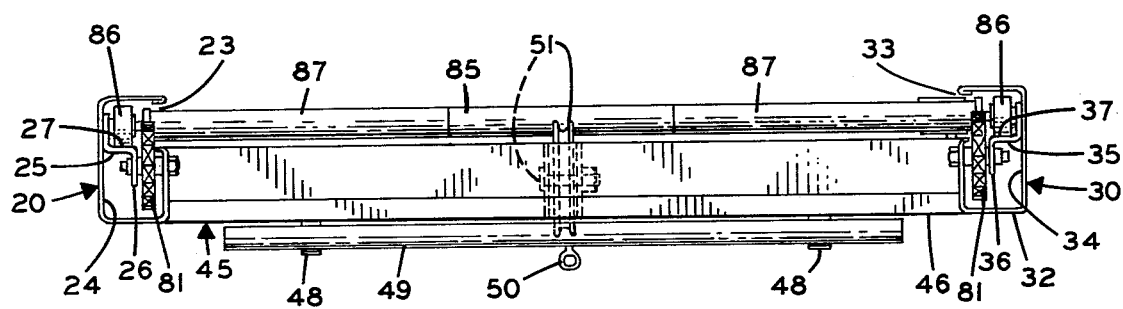
FIG. 4 is a somewhat enlarged top plan view of the apparatus taken from a position indicated by line 4—4 in FIG. 1.
Figure 5:
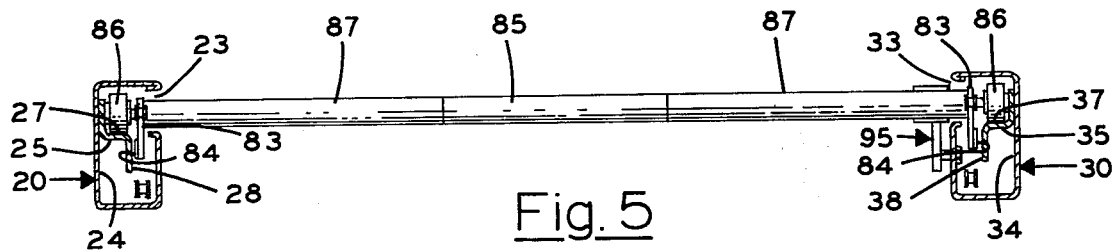
FIG. 5 is a transverse section taken on line 5—5 in FIG. 1.
Figure 15:
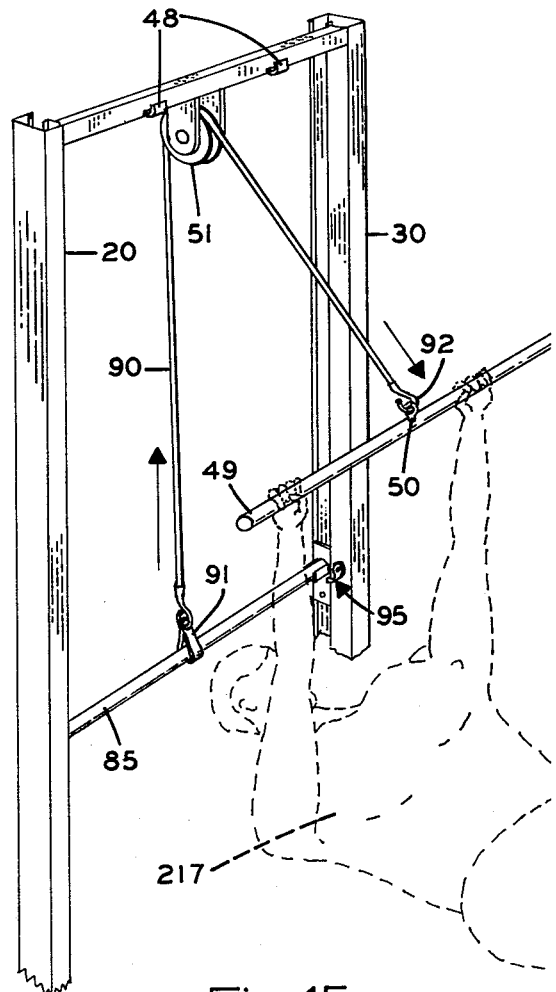
FIG. 15 is a fragmentary perspective view of the apparatus assembled in an alternate configuration for purposes of exercising.

The frame 11 has a first column or frame member 20 on the left, as viewed in FIGS. 1, 3, 4 and 5, and on the right as viewed in FIGS. 8 and 10. The first frame member has a proximal end 21 which is secured, as by welding, on the opposite end 16 of the channel member 15 on the left as viewed in FIG. 1 and in right-angular relation thereto. The frame member has a distal end 22 and is in cross section roughly of rectangular tube construction, but has a slot 23 extending longitudinally thereof interconnecting the proximal and distal ends 21 and 22 thereof, as best shown in FIGS. 4, 5 and 15. The slot thus communicates with the interior of the frame member throughout its length. The frame member has an interior surface 24. A guide member 25 is affixed on the interior surface 24 of the frame member 20 extending substantially the entire length thereof through the interior of the member in the position opposite the slot 23 thereof shown in FIGS. 4 and 5. The guide member has a remote end 26 substantially coterminous with the distal end 22 of the frame member 20. The guide member has a central track surface 27 and a right angularly related stabilizing surface 28 which extend the full length of the guide member.

Figure 6:
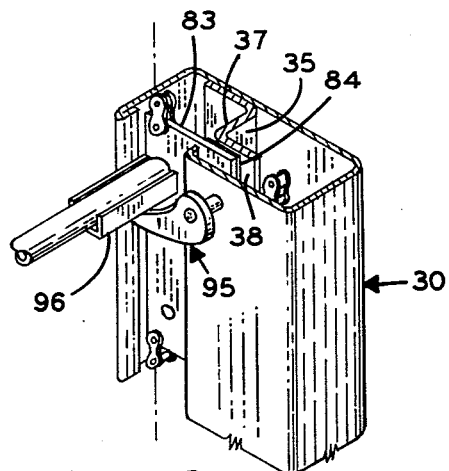
FIG. 6 is a somewhat further enlarged fragmentary perspective view of a portion of one of the vertical columns of the apparatus showing the latching mechanism thereof.

The frame 11 has a second column or frame member 30 on the right, as viewed in FIGS. 1, 3, 4 and 5, and on the left as viewed in FIGS. 8 and 10. The frame member has a proximal end 31 secured, as by welding, on the opposite end 16 of the channel member 15 on the right, as viewed in FIG. 1, and right-angularly related to the channel member. The frame member has a distal end 32 remote from the proximal end. The frame members 20 and 30 are extended in parallel relation from the transverse channel member 15, as shown in FIG. 1. The second frame member 30 has a slot 33 extending substantially the entire length thereof, as best shown in FIGS. 4, 5 and 16. The frame member 30 has an interior surface 34 with a guide member 35 fastened, as by welding, on the interior surface of the frame member 30 and extending substantially the entire length thereof opposite the slot 33. The guide member 35 has a remote end 36 substantially coterminous with the distal end 32 of frame member 30. The guide member has a track surface 37 and a right angularly related stabilizing surface 38, as best shown in FIGS. 4 through 6. Both surfaces extend the full length of the guide member.

A transverse brace member 45 is fastened on and interconnects the distal ends 22 and 32 of the frame members 20 and 30 respectively so as to be substantially parallel to the channel member 15. The brace member 45 is substantially L-shaped in cross section and has a front surface 46 and a lower surface 47. A pair of hooks 48 are mounted in spaced relation on the front surface of the brace member as best shown in FIGS. 1 and 4. An auxiliary exercising bar 49 is removably received in the hooks 48. A ring 50 is secured substantially centrally of the bar 49. A pulley assembly 51 is mounted on the lower surface 47 of the brace member 45, as shown in FIGS. 1 and 15.

A first support housing 55 is fastened, as by welding, on the side 14 of the platform 12 on the left, as viewed in FIGS. 1 and 3. The housing is weldably secured to and thus supports the first frame member 20. The support housing has a sloping surface 56 which slopes from the frame member to the floor 13 of the platform 12 and rearwardly to a position in juxtaposition to the pump platform 17. The surface 56 has a recess 57 therein in alignment with the slot 23 of the frame member 20. A resilient rest 58 is secured in the recess, as best shown in FIGS. 1, 3 and 10, in alignment with the slot 23 of the frame member 20. The housing has a flat mounting plate 59 which is mounted on and extends along the back of the first frame member 20, as can best be seen in FIGS. 9 and 10. Suitable braces, not shown, can be mounted within the housing to reinforce the frame member 20 from the channel member 15.

A second support housing 65 is affixed on the side 14 of the platform 12 opposite that connecting with the first support housing 55. The second support housing has a sloping surface 66 which slopes from the second frame member 30 at an angle to the floor 13 of the platform. The sloping surface has a recess 67 therein in alignment with the slot 33 of the second frame member. A resilient rest 68 is mounted in the recess on the housing, as can best be seen in FIGS. 8 and 10.

The apparatus 10 has a drive assembly 75 mounted on the frame 11 and best shown in FIGS. 1 through 5 and 10. The drive assembly has a pair of bearings 76 individually mounted on the frame members 20 and 30 adjacent to the proximal ends 21 and 31 respectively thereof in axial alignment, thus shown in FIG. 10. A shaft 77, having opposite ends 78, is rotationally received in the pair of bearings 76 having the end 78 thereof on the right, as viewed in FIG. 10, extended through the bearing externally of frame member 20. A pair of sprockets 79 are secured in spaced relation on the shaft 77 for rotation therewith and in individual vertical alignment with the interiors of the frame members 20 and 30 respectively, as best shown in FIG. 10. An outer sprocket 80 is affixed for rotation with the shaft 77 on the end thereof on the right, as viewed in FIG. 10. A pair of upper sprocket assemblies 81 are individually mounted on the frame members 20 and 30 adjacent on the distal ends 22 and 32 respectively thereof. The sprocket assembly 81 shown on the left in FIG. 4 is mounted between the remote end 26 of the guide member 25 and the frame member 20. The sprocket assembly 81 on the right in FIG. 4 is mounted on the remote end 36 of the guide member 35 and the frame member 30.

A pair of drive chains 82 are individually extended about and engaged on the sprocket 79 and sprocket assembly 81 of the frame members 20 and 30 respectively. Each drive chain has a mounting plate 83 secured thereon which is received within its respective frame member just inwardly of its respective slot 23 or 33, as best shown in FIGS. 5 and 6. Each mounting plate has a Nylon or Teflon pad 84 fastened on the side thereof remote from its respective slot for sliding engagement with its respective stabilizing surface 28 or 38 of the guide members 25 and 35 respectively. A cross member or bar 85 is secured on and thus interconnects the mounting plates 83 in substantially parallel relation to the channel member 15 and brace member 45. Each mounting plate also mounts a wheel assembly 86 which is disposed for rolling engagement with the respective track surface 27 or 37 of the guide members 25 and 35. A pair of sleeves 87 are rotationally received on a cross bar, as best shown in FIG. 1.

An auxiliary cable 90 is shown in FIG. 15. The cable has a strap assembly 91 at one end thereof and an attachment hook 92 at the other end. The cable is adapted to be extended through the pulley assembly 51. The strap assembly 91 is designed to be attached to the cross bar and the hook 92 to be attached to the ring 50 for adaptation of the apparatus 10 to other forms of exercising, such as shown in FIG. 15.

Figure 7:
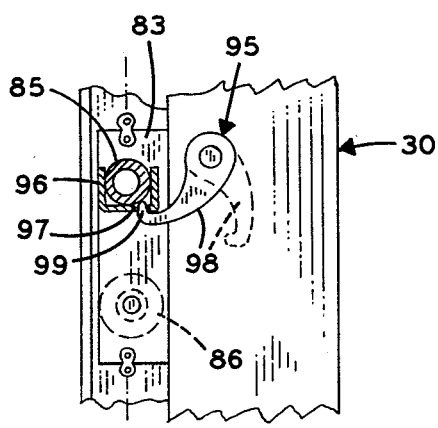
FIG. 7 is a fragmentary side elevation of the column of FIG. 6 showing the latching mechanism thereof.

A latch assembly 95 is borne by the second frame member 30, as best shown in FIGS. 6 and 7. The latch assembly includes a channel member 96 which is fastened on the cross bar mounting plate 83 of the second frame member and is extended outwardly therefrom under the cross bar 85. The channel member has a hole 97 on the under side thereof in the position shown. A latch arm 98 is pivotally mounted on the second frame member and has an end portion or prong 99 adapted to be received in the hole of the channel member as shown in FIG. 7 to retain the cross bar in a "ready" or "start" position.

Figure 9:
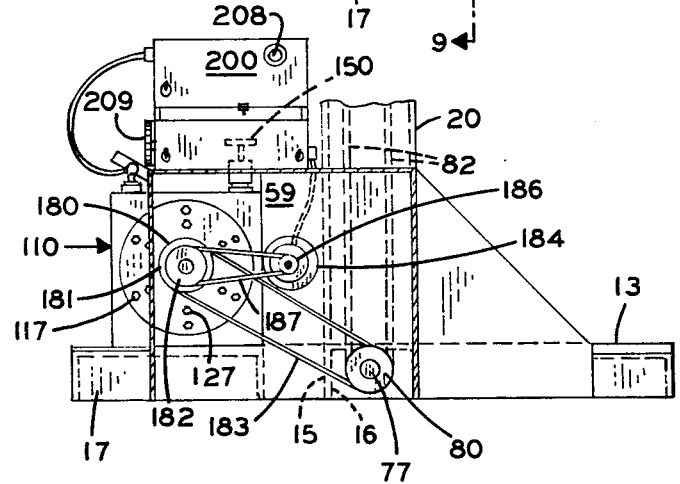
FIG. 9 is a somewhat enlarged fragmentary transverse vertical section taken on line 9—9 in FIG. 8.

A resistance mechanism or fluid pump 110 is mounted on the pump platform 17, and is best shown in FIGS. 9, 10 and 11. The pump has a fluid tight housing 111 composed of a floor 112 having upstanding side walls 113 and a top wall 114 defining an internal fluid reservoir 115 for the fluid pump. A mounting plate 116 is secured on the side wall on the right, as viewed in FIG. 11, by mounting bolts 117. The mounting plate has a central bearing 118. The top wall has a fluid filler opening 119 in which a plug 120 is removably received.

A piston pump 125 is borne by the side wall 113 mounting the mounting plate 116 and is in axial alignment with the central bearing 118 thereof within the fluid reservoir 115 of the fluid housing 111. The piston pump has a pump casing or housing 126 which is secured in position on the side wall and interconnected with the mounting plate 116 through mounting bolts 127. The pump housing 126 encloses wobble plate chamber 128 between the side wall and the pump housing. The housing has a plurality of cylinders 129 formed therein extending from the wobble plate chamber into the housing parallel to the axis of the central bearing 118 and defining an annular pattern substantially concentric to the axis of the central bearing. Although there may be a greater or lesser number of cylinders, eight such cylinders are preferred for smooth, dependable operation of the apparatus. Each of the cylinders has a piston 130 received therein for reciprocal movement between an extended position, as shown in FIG. 11, and a retracted position more fully received within its respective cylinder. A compression spring 131 is received within each of the cylinders 129 disposed between the piston 130 of that cylinder and the interior end of the cylinder, as shown in FIG. 11. The compression springs operate to urge the pistons of those cylinders to the extended positions shown in FIG. 11.

An exhaust fluid passage 132 is extended through the housing 126 from the interior end of each cylinder longitudinally of the pump housing 126 substantially parallel to the axis of the central bearing 118. The exhaust fluid passages 132 are interconnected adjacent to the interior end of the pump housing by an annular passage 133 substantially concentric to the axis of the central bearing. An exhaust check valve assembly 134 is operably mounted within each of the exhaust fluid passages extending through the annular passage. Each check valve assembly is operable upon fluid pressure being exerted thereagainst, as will hereinafter be described, selectively and individually to admit the fluid to the annular passage from its respective exhaust fluid passage.

A central intake passage 135 is provided in the pump housing 126 extending from the interior end of the pump housing inwardly of the housing a predetermined distance in coaxial relation with the central bearing 118, as shown in FIG. 11. An intake fitting 136 is secured on the housing in communication with the intake passage and bent, as shown in FIG. 11, in the direction of the floor 112 of the fluid housing 111. A radial intake passage 137 individually interconnects the interior end of the central intake passage 135 with each of the exhaust fluid passages 132.

An intake check valve assembly 138 is mounted within each radial intake passage 137 in communication with its respective exhaust fluid passage. The intake check valve is operable, as will hereinafter be described, to admit fluid drawn in through the intake passage 135 to its respective exhaust fluid passage 132 upon movement of the piston of its respective cylinder to the extended position shown in FIG. 11.

A main shaft 139 is rotationally received in the central bearing 118 of the mounting plate 116. A bearing 140 is affixed on the housing 126 and mounts the interior end of the shaft 139 therein for rotational movement. A wobble plate assembly 141, of known construction, is secured on the shaft within the chamber 128 for rotational movement with the shaft. The assembly includes a piston contact plate 142 which is borne by the shaft 139 at a diagonal angle adjacent to the pistons 130. In the conventional fashion rotation of the main shaft 139 and wobble plate assembly causes the piston contact plate to be motivated in a swivel motion which causes selective, sequential depression of the pistons 130 thereby operating the piston pump 125.

A resistance control valve 150 is mounted on the top wall 114 of the fluid housing 111. The valve assembly has a valve housing 151 enclosing a valve passage 152 of a conventional configuration extending therethrough. The valve has a valve closure 153 mounted for screwthreaded adjustment and operable to close or incrementally open the valve passage through the housing. The closure has a handle 154 for selective adjustment of the valve as described. A first conduit 155 interconnects in fluid transferring relation the annular passage 133 of the piston pump and the upstream side of the valve housing 151. A second conduit 156 interconnects the downstream side of the valve housing and extends downwardly within the fluid reservoir 115 of the fluid housing 111. For illustrative convenience, hydraulic fluid is indicated at 157 within the fluid reservoir of the fluid housing.

A pressure registering assembly 170 is fastened on the top wall 114 of the fluid housing 111. The pressure registering assembly includes a pressure conduit assembly 171 connected at one end to the annular passage 133 of the pump housing 126 and mounted at the other end on the top wall 114. A pressure release valve 172 is operably secured on the conduit in the conventional fashion. The release valve is operable to release pressure from the conduit assembly when the fluid pressure within the conduit, and thus within the piston pump 125, reaches a predetermined upper limit. An exterior fitting 173 is affixed on the conduit assembly externally of the fluid housing 111 in fluid conducting relation. A pressure gauge 174 is borne by the fitting, as shown in FIG. 11, and adapted to register pressure produced within the conduit assembly and thus the piston pump. A pressure transducer 175 is mounted on the other side of the fitting, as shown in FIG. 11, in communication with fluid within the conduit assembly and fitting.

A drive assembly including a one way clutch 180 is operatively mounted on the main shaft 139 of the piston pump 125. The clutch mounts a sprocket 181 which is operable with the clutch to rotate the main shaft to operate the piston pump only when the sprocket is rotated in a driving mode constituting movement in a clockwise direction, as viewed in FIG. 9. If the sprocket is rotated in the opposite direction the clutch operates to release the shaft thereby allowing the sprocket simply to rotate while the main shaft remains stationary. A sprocket 182 is mounted on the remote end of the main shaft 139. A drive chain 183 is extended about the sprocket 181 and the outer sprocket 80 of shaft 77. Thus, it will be seen that upward movement of the cross bar 85 causes the sprocket 80, drive chain 183 and sprocket 181 to be rotated in clockwise directions, as viewed in FIG. 9. This, as previously described, causes the clutch 180 to operate to engage the main shaft 139 and thereby to operate the piston pump 125.

A selsyn generator 184 is mounted on the mounting plate 59, as shown in FIGS. 9 and 10. The selsyn generator has a drive shaft 185 mounting a sprocket 186 adapted for rotation with the drive shaft 185. A drive chain 187 is extended about and operably interconnects sprocket 182 of main shaft 139 and sprocket 186 of drive shaft 185. Thus, it will be seen that rotation of the main shaft 139 by upward movement of the cross bar 85 causes the sprocket 182, drive chain 187, sprocket 186 and drive shaft 185 all to be rotated in a clockwise direction, as viewed in FIG. 9, and therefore to operate the selsyn generator 184. Conversely, when the cross bar is retained in position or moved downwardly, the selsyn generator is not operated as a result of the one way clutch 180.

A strip chart recorder 200 for the apparatus 10 is best shown in FIG. 12. The recorder can be of any one of a variety of conventionally available types modified as will herein be described in accordance with the present invention. For example, a Varian Associates Graphic Recorder Model G-10 can be employed for this purpose. For purposes of illustrative convenience, it will be sufficient to state that the recorder is of any suitable type, conventional or otherwise and has a housing 201 with a chart discharging opening 202 therein. A pen mounting bar 203 is affixed on the housing extending above the opening 202. In the conventional manner a pen 204 is borne for slidable movement along the bar as controlled by the operation of the recorder. An "on-off" switch for the recorder is indicated at 205. A pen travel or servo control switch conventionally employed on many strip chart recorders is indicated at 206. Similarly, a chart drive "on-off" switch is indicated at 207.

The modifications and additions to the strip chart recorder 200 embodied in the apparatus of the present invention include a span adjustment dial or switch shown at 208. The span adjustment switch preferably has two positions. One position preferably sets the recorder to record its results on a chart in a range of between 0 and 500 pounds force exerted upwardly against the cross bar 85. A second position registers the results in a range of from 0 to 1000 pounds force exerted against a cross bar in an upward direction. Thus, for example if the span adjustment switch 208 is set at the 0 to 500 pounds position, the width of the strip chart covers a range of from 0 to 500 pounds force exerted on the bar with the maximum distance of pen travel on the strip chart corresponding to 500 pounds. Similarly the 0 to 1000 pounds position sets a range of from 0 to 1000 pounds against which the results are recorded. The strip chart recorder 200 shown in FIG. 12 has a manual chart feed gear or wheel 209 connected in the conventional manner to the chart drive assembly, not shown, of the recorder and operably to feed the chart therefrom.

Other modifications of the recorder 200 include a selsyn motor 210 mounted within the housing 201 of the recorder. The selsyn motor is coupled by means of a gear, not shown, to the chart feed gear or wheel 209. A suitable ratio between the gears can be employed to achieve a chart drive ratio of movement to movement of the cross bar 85, as will hereinafter be set forth. A 10-volt, D.C. power supply, preferably in the form of batteries, is indicated at 211 mounted within the housing 201. A main electrical supply cord 212 to provide power for the strip chart recorder is operably extended from the back of the recorder, as shown in FIG. 1, for connection to a suitable source of electrical energy. A pressure transducer cord 213 interconnects the pressure transducer 175 and the housing 201, as shown in FIGS. 11 and 12. The 10-volt power supply 211 is electrically connected to the transducer through the cord 213 and in series relation the pressure transducer is then connected to the recorder in the conventional fashion to control movement of the pen 204 along the bar 203. The power supply 211 is necessary to provide excitation voltage to the transducer for proper operation thereof.

A selsyn generator cord 214 operatively interconnects the selsyn generator 184 and the selsyn motor 210. The selsyn motor is thus wired to the selsyn generator in such a manner that it operates only when the generator is operated and at the same speed, as previously described. Thus, for example, a one inch upward movement of the cross bar 85 advances the chart through the recorder by way of the selsyn generator and selsyn motor a predetermined equivalent of one inch. A suitable ratio for movement of the chart in relation to movement of the bar has been found to be one to ten. Where so adjusted, a one inch movement of the cross bar 85 in an upward direction will move the chart one-tenth of one inch. For illustrative convenience, a strip chart 215 is shown in FIG. 12 in the strip chart recorder in an operative condition. Also for purposes of illustrative convenience, a bench 216 is shown in dashed lines in a typical operating position in FIG. 1. An operator 217 is shown in dashed lines in FIG. 1 on the bench in a typical position for operation of the apparatus. The operator 217 is shown in dashed lines in an alternate position in FIG. 15.

A portion of a representative strip chart 200 is shown in FIG. 13. The strip chart 220 represents the recorded results of one complete upward stroke of the cross bar 85 by an operator having exerted approximately 300 pounds force against the bar at the end of the stroke with the span adjustment dial 208 having been set in the 0 to 500 pounds position. The strip chart 220 has a line 221 thereon representing the stroke. For illustrative convenience, the line may be viewed as having a first portion 222 illustrative of the force exerted by the operator at the beginning of the stroke, a middle portion 223 illustrative of the lack of strength of the operator during the midpoint of the stroke and a last portion 224 illustrative of the maximum power exerted by the operator toward the end of the stroke.

A portion of a second representative strip chart 225 is shown in FIG. 14 displaying a line 226. The line has a first portion 227 and a middle portion 228 which, in comparison with the strip chart 200 indicates improvement typical of use of the apparatus 10 of the present invention. A last portion of the line is indicated at 229.

OPERATION

The operation of the described embodiment of the subject invention is believed to be readily apparent and is briefly summarized at this point. The exercising apparatus 10 can be operated in virtually any of the conventionally utilized exercising attitudes. For example, as shown in FIG. 1, the operator 217 is performing what is referred to as the "bench press" wherein he rests on his back on a bench 216 and performs, in effect, a weightlifting operation. The most common conventional means by which this bench press operation can be performed is simply by having the operator lift weights from the position shown. Where such barbell type weights are employed, the operation is quite dangerous in view of the fact that the barbell if dropped may fall on the operator causing serious injury. The apparatus of the present invention entirely avoids this risk of injury while providing a host of additional operative advantages not found in conventional devices.

To activate the apparatus, the main electrical supply cord 212 is plugged into an outlet of a suitable source of electrical energy to provide for the operation of strip chart recorder. The switches 205, 206 and 207 are switched "on" to make the recorder, pen and chart drive operable. Similarly, the span adjustment dial 208 is set at the desired position.

Using the exercising position shown in FIG. 1, the operator simply "lifts" the cross bar 85 by pushing it away from his body. Initial movement of the cross bar causes the latch assembly 95 to operate whereby the channel member 96 is drawn away from the prong 99 of the latch arm 98 thereby causing the latch arm gravitationally to rotate to the retracted position shown in dashed lines in FIG. 7. In this retracted position the latch arm does not interfere with further operation of the cross bar in the exercising operation.

As previously described and as can best be seen in FIGS. 2, 9 and 10, upward movement of the cross bar 85 causes the pair of drive chains 82 to be motivated about their respective sprockets 79 and 81 in clockwise directions, as viewed in FIG. 2. Similarly, the outer sprocket 80, the drive chain 183, and the sprocket 181 are rotated in a clockwise direction, as viewed in FIG. 9. As previously described, rotation in this direction operates the one way clutch 180 to cause the main shaft 139 of the piston pump 125 to be rotated in a clockwise direction, as viewed in FIG. 9.

As a result the wobble plate assembly 141 carries the piston contact plate 142 into sequential engagement with the pistons 130. Consequently, the pistons are sequentially depressed against their respective compression springs 131 in the conventional manner. It will be seen that on depression of a piston, hydraulic fluid 157 within the exhaust fluid passage 132 thereof is forced along the passage, against its valve assembly 134 and is admitted to the annular passage 133 of the pump housing 126. Such sequential operation of the pistons thereby causes the hydraulic fluid to be pumped in a smooth and steady stream into the annular passage, along the first conduit 155, through the valve passage 152 which has been preset by the operator utilizing the handle 154 of the resistance control valve assembly 150. Fluid pressure is thus created within the conduit 155, the annular passage 133, the pressure conduit assembly 171 and the fitting 173.

It will thus be seen that upward movement of the cross bar 85 is restrained by the fluid pressure generated within the fluid pump 110. The appropriate selection for the setting of the handle 154 assists in controlling the actual amount of pressure created to resist such upward movement thereby permitting the operator to select the amount of resistance desired. The pressure release valve 172 operates to release fluid pressure from the pressure conduit assembly 171 and thus the pump 110, upon fluid pressure having reached a preselected upper limit, in order to prevent damage to the pump. Hydraulic fluid 157 is drawn into the piston pump 125 by sequential movement of the piston 130 to the extended positions shown in FIG. 11 upon release by the piston contact plate 142. The vacuum created in each cylinder 129 by the movement of the piston thereof to the extended position operates its respective intake check valve assembly 138 to admit hydraulic fluid through the intake fitting 136, the intake passage 135, its respective radial intake passage 137, the intake check valve assembly 138 and into the exhaust fluid passage 132 to fill the available space created by pumping of the hydraulic fluid through check valve 134 prior thereto.

The pressure gauge 174, in contact with fluid within the fitting 173 operates visibly to register the pressure created within the fluid pump 110. Similarly, the pressure transducer 175 borne by the fitting 173, under excitation by the 10-volt power supply 111 connected thereto by the pressure transducer cord 213 operates to create an electric signal registering such pressure created within the fluid pump 110. This signal is carried along the pressure transducer cord 213 back to the strip chart recorder 200 to control movement of the pen 204 on the pen bar 203.

Simultaneously the operation of the selsyn generator 184 by way of the sprocket 182, drive chain 187, sprocket 186 and drive shaft 185 causes electrical energy to be generated and carried through the selsyn generator cord 214 to the strip chart recorder to supply electrical energy to the selsyn motor 210. As previously described the selsyn motor operates the strip chart recorder to feed the strip chart 215 from the recorder at a rate of speed corresponding to the actual distance of movement of the cross bar 85. It will be seen that the amount of force exerted against the bar by the operator in an upward direction is recorded on the strip chart in relation to the actual distance traveled by the bar. Thus, a line, such as shown at 221 and 226 in FIGS. 13 and 14 respectively, is produced which serves as a record of the force exerted by the operator against the bar at each point of upward travel of the cross bar.

When the cross bar 85 is drawn or released for movement in a downward direction in the frame 11, the one way clutch 180 operates to release the main shaft 139 so as not to operate the fluid pump 110 nor the strip chart recorder 220. The cross bar thus freewheels in a downward direction in an unweighted condition and there is no danger of the cross bar in a weighted condition falling on the operator so as to cause injury. Furthermore, due to the release by the one way clutch, the cross bar can be immediately returned to the "start" position for immediate repetition of the exercising operation.

As can be seen in FIGS. 4, 5 and 6, the cross bar mounting plates 83 utilizing the nylon or Teflon pads 84 and the wheel assemblies 86 operate to provide smooth and dependable movement of the cross bar 85 within the frame 11. As previously noted, the eight piston pump 125 has been found to provide a smoothness of operation so that upward movement of the bar is also smooth. The sleeves 87 which are gripped by the operator 217 permit the operator to rotate his hands relative to the cross bar 85 so as to assume the most comfortable position with respect thereto during the lifting operation. When the operator has completed the exercising operation he can operate the latch assembly 95 by simply pivoting the latch arm 98 to insert the prong 99 thereof in the hole 97 of the channel member 96 thereby retaining the cross bar 85 in the "start" position shown in FIG. 1.

An alternate configuration for operation of the apparatus 11 is illustrated in FIG. 15. This arrangement permits the operator to exercise against a resistance force by movement in downward or diagonal directions rather than the upward direction heretofore described.

This configuration is accomplished by extending the auxiliary cable 90 through the pulley assembly 51, as shown in FIG. 15. The strap assembly 91 is then fastened to the cross bar 85 as shown in FIG. 15 and the hook 92 is inserted through the ring 50 of the auxiliary exercising bar 49. The operator 217 can then either stand or lie in a prone position and pull downwardly or diagonally on the auxiliary exercising bar 49 so as to raise the cross bar 85 and the frame 11 to accomplish the operation of the apparatus 10, as previously described. This permits rapid and effective exercising without the risk of injury of the type previously described.

Referring more particularly to FIG. 13, the line 221 shown therein illustrates an actual and fairly typical single upward stroke of the cross bar 85 by an operator 217 who has exercised with weights so as to permit lifting of weight up to 300 pounds in a "bench press" operation. However, the middle portion 223 of the line illustrates that the operator has a weak point midway through the upward stroke which corresponds to the position of the arms approximately midway through an upward stroke.

In conventional weightlifting operations there is no opportunity for the operator to improve upon this weak point since conventional exercising devices have no means for registering this weak point for comparative improvement. However, by continuing to exercise through this weak point the operator can achieve considerable improvement, as illustrated in FIG. 14. The line 226 shown on the representation portion of the strip chart 225 illustrates that the weak point indicated at middle portion 228 is vastly improved over that indicated by the line 221 on chart 220 in FIG. 13 for that operation. This capability for improving upon the strength of the operator at any selected point throughout the stroke has considerable value for both athletic and therapeutic purposes. Stating the same proposition another way, the operator of chart 225 can lift approximately 85 pounds more than the operator of chart 220 at their respective weakest points. This is because the operator of chart 225 has been lifting weights and strengthened this weak point. Since a weight lifter using barbells cannot lift more weight than he can get through this weak point, the operator of chart 225 can lift greater weight using barbells than the operator of chart 220.

The exercising apparatus effectively varies its resistance as the operator's strength varies throughout his lifting stroke. This is because of the use of the valve assembly 150 having a restricted valve passage 152. Once the closure 153 has been set, the more force is applied to the cross bar 85 the more restraint to movement of the cross bar is, in effect, created by the fixed capacity of the passage. The application of less force to the cross bar produces a corresponding reduction in the effective resistance produced by the apparatus to such movement. Consequently, the apparatus can be operated to demand 100 percent of the strength of the operator throughout the entire stroke.

Therefore, the exercising apparatus of the present invention is a convenient, safe and fully adaptable device which offers resistance to exercising force varying in direct relation to the force applied permitting the operator to work at his maximum ability throughout the lifting stroke while simultaneously operating automatically to produce a physical record of the force exerted in correlation to the position of the exercising member throughout the lifting stroke.

Although the invention has been herein shown and described in what is conceived to be the most practical and preferred embodiment, it is recognized that departures may be made therefrom within the scope of the invention, which is not to be limited to the illustrative details disclosed.

Having described my invention, what I claim as new and desire to secure by Letters Patent is:

1. An exercising apparatus comprising a movable member provided for the application of muscular force thereto; a fluid pump adapted to receive fluid and having a plurality of pistons adapted to pump said fluid; a wobble plate borne by the pump for swiveling movement and sequentially engageable with the pistons to pump fluid substantially constantly during said swiveling movement; rotary means operatively connected to the wobble plate for rotation to cause said swiveling movement of the wobble plate; and a linkage interconnected the rotary means and the member for rotation of said rotary means only when the member is moved in a single direction of movement and accommodating substantially resistance free movement in the opposite direction.

2. The apparatus of claim 1 wherein the resistance means further includes a valve connected to the fluid pump in fluid receiving relation and adjustable to control resistance of the valve to pumping of the fluid therethrough to create a fluid pressure within the pump resisting movement of the member in the single direction.

3. The apparatus of claim 2 including means connected to the resistance means for registering the fluid pressure developed within said resistance means as an indication of the force applied to said member.

4. An exercising apparatus comprising a frame, a pair of endless chains mounted on the frame for movement along substantially parallel paths of travel, a shaft assembly interconnecting corresponding portions of said pair of chains for rotation by said pair of chains during said movement thereof, a bar interconnecting corresponding portions of said pair of chains in substantially right-angular relation thereto for the application of force thereagainst to cause movement of said pair of chains and the shaft assembly, a fluid system having fluid therein, a fluid pump connected to the system operable to pump fluid through said fluid system to develop a fluid pressure, a one way clutch interconnecting the fluid pump and the shaft assembly operable to drive the pump only when the shaft assembly is rotated in a predetermined direction whereby the fluid pressure developed during said operation of the fluid pump resists rotation of the shaft assembly during movement of the chains and bar in one direction along the paths of travel, a pressure transducer operable to detect said fluid pressure, a chart recorder electrically connected to the pressure transducer and operable to record said fluid pressure detected by the transducer on a chart, a selsyn generator connected in driven relation to the one way clutch and operable to generate electrical energy, a selsyn motor connected to the recorder and operable to feed a chart through the recorder, electrical conducting means interconnecting the generator and the motor to supply electrical energy generated by the generator to the motor for operation thereof whereby movement of the bar a given distance in said one direction feeds the chart through the recorder a distance corresponding to said given distance, a power source electrically connected to the pressure transducer to provide excitation voltage sufficient to operate the transducer, means for interconnecting the pressure transducer and the selsyn motor with the recorder so that movement of the bar in said one direction operates to record the fluid pressure developed within the fluid pump as an index of force exerted against the bar opposite a first axis on the chart and simultaneously the distance corresponding to said given distance of movement of the bar opposite a second axis on the chart to product a graph on the chart indicating the force applied to the bar for every position of the bar during movement in said one direction, and a latch assembly mounted on the frame for pivotal movement between an extended position in releasable engagement with the bar in a ready position and a position gravitationally retracted therefrom.

5. The apparatus of claim 4 wherein the frame is adapted to be operated in an upright attitude, said one direction of movement of the bar is in an upward direction in the frame and the apparatus includes a pulley assembly mounted on the frame above the bar, and an auxiliary exercising assembly adapted to be connected to the bar, extended through the pulley assembly and downwardly therefrom for movement in a downward direction to operate said fluid pump.

6. In an exercising apparatus having a frame, a member borne by the frame for movement in opposite directions along a substantially upright path of travel, means including a fluid pump operably connected to the member for resisting movement of the member in an upward direction along the path of travel for the application of muscular force to the member in said upward direction against the action of the resisting means, the improvement comprising a latch assembly pivotally mounted on the frame for movement between a raised position in said path of travel and a lowered position out of said path of travel and said latch assembly having an end portion engageable with the member in the raised position to retain the member in a ready position and releasable therefrom by upward movement of said member for gravitational movement of the latch assembly to the lowered position.

7. An exercising apparatus comprising a fluid system containing a fluid, a fluid pump having a plurality of pistons connected to the system and adapted for operation to pump fluid through the system developing a fluid pressure within said system resistant to operation of the pump, a drive assembly linked to the pump and operating the pump only when said assembly is operated in a driving mode, a substantially upright frame, a member mounted on the frame for movement along a substantially upright path of travel, and means interconnecting the member and the drive assembly and operating the drive assembly in said driving mode only when the member is moved in an upward direction along the path of travel and permitting substantially unrestricted gravitational movement in a downward direction along the path of travel.

8. The apparatus of claim 7 including means connected to the apparatus for registering the force applied to the member in said upward direction in relation to the position of the member along said path of travel.

9. The apparatus of claim 7 wherein said drive assembly includes a clutch which permits substantially unrestricted movement of the member when said member is moved in other than said upward direction.

10. An exercising apparatus comprising a fluid system containing fluid, a fluid pump connected to the system and having a plurality of pistons and adapted for operation to pump fluid through the system developing a fluid pressure within said system resistant to operation of the pump, a drive assembly linked to the pump and operating the pump only when said assembly is operated in a driving mode, a member for the application of force thereto movable along a path of travel, and means interconnecting the member and the assembly and operating the assembly in said driving mode only when the member is moved in a predetermined direction along the path of travel.

11. The apparatus of claim 10 wherein the drive assembly is connected to the pump so as to operate the pistons of the pump at a speed in relation to the force exerted in moving the member in said predetermined direction to create relatively greater and alternatively lesser resistance to movement of the member corresponding to the force applied to said member.

12. The apparatus of claim 10 wherein said drive assembly includes a wobble plate borne by the apparatus for sequential operation of the pistons of the pump upon operation of said assembly in the driving mode.

* * * * *

UNITED STATES PATENT AND TRADEMARK OFFICE
CERTIFICATE OF CORRECTION

PATENT NO. : 4,050,310
DATED : September 27, 1977
INVENTOR(S) : Dennis L. Keiser It is certified that error appears in the above-identified patent and that said Letters Patent are hereby corrected as shown below:

Column 9, Line 34, delete "200" and substitute --- 220 ---.

Line 52, delete "200" ans substitute --- 220 ---.

Column 10, Line 9, insert --- power --- between "provided" and "for".

Column 11, Line 40, delete "220" and substitute --- 200 ---.

Line 65, delete "11" and substitute --- 10 ---.

Column 12, Line 30, delete "representation" and substitute --- representative ---.

Column 14, Line 9, delete "product" and substitute --- produce ---.

Signed and Sealed this

Twenty-first Day of March 1978

[SEAL]

Attest:

RUTH C. MASON
Attesting Officer

LUTRELLE F. PARKER
Acting Commissioner of Patents and Trademarks